US00PP16236P2

(12) United States Plant Patent
Schräder

(10) Patent No.: US PP16,236 P2
(45) Date of Patent: Feb. 7, 2006

(54) ***DIASCIA* PLANT NAMED 'SUMDIA 02'**

(50) Latin Name: *Diascia elegans*
Varietal Denomination: Sumdia 02

(76) Inventor: Ralf Schräder, Karl-Leisner-Str. 15, D-59348 Lüdinghausen (DE)

( * ) Notice: Subject to any disclaimer, the term of this patent is extended or adjusted under 35 U.S.C. 154(b) by 46 days.

(21) Appl. No.: 10/968,784

(22) Filed: Oct. 19, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—C. A. Whealy

(57) ABSTRACT

A new and distinct cultivar of *Diascia* plant named 'Sumdia 02', characterized by its compact, upright and outwardly spreading plant habit; freely branching habit; freely and early flowering habit; intense red-colored flowers; and good temperature tolerance.

2 Drawing Sheets

Botanical classification/cultivar designation: *Diascia elegans* cultivar Sumdia 02.

BACKGROUND OF THE INVENTION

The present Invention relates to a new and distinct cultivar of *Diascia* plant, botanically known as *Diascia elegans,* and hereinafter referred to by the cultivar name Sumdia 02.

The new *Diascia* is a product of a planned breeding program conducted by the Inventor in Lüdinghausen, Germany. The objective of the breeding program is to create new early flowering *Diascias* with numerous flowers, attractive flower coloration and long flowering period.

The new *Diascia* originated from a cross-pollination made by the Inventor in May, 2002 of a proprietary seedling of *Diascia elegans* identified as code number 14, not patented, as the female, or seed parent, with a proprietary seedling of *Diascia elegans* identified as code number 2, not patented, as the male, or pollen parent. The new *Diascia* was selected as a single plant from the resulting progeny of the cross-pollination by the Inventor in June, 2003, in an controlled environment in Lüdinghausen, Germany.

Asexual reproduction of the new cultivar by terminal cuttings in a controlled environment in Lüdinghausen, Germany since June, 2003, has shown that the unique features of this new *Diascia* are stable and reproduced true to type in successive generations.

SUMMARY OF THE INVENTION

Plants of the cultivar Sumdia 02 have not been observed under all possible environmental conditions. The phenotype may vary somewhat with variations in environment such as temperature and light intensity without, however, any variance in genotype.

The following traits have been repeatedly observed and are determined to be the unique characteristics of 'Sumdia 02'. These characteristics in combination distinguish 'Sumdia 02' as a new and distinct cultivar of *Diascia:*

1. Compact, upright and outwardly spreading plant habit.
2. Freely branching habit.
3. Freely and early flowering habit.

4. Intense red-colored flowers.
5. Good temperature tolerance.

Plants of the new *Diascia* differ from plants of the female parent selection in the following characteristics:

1. Plants of the new *Diascia* flower for a longer period of time than plants of the female parent selection.
2. Plants of the new *Diascia* have darker colored flowers than plants of the female parent selection.

Plants of the new *Diascia* differ from plants of the male parent selection in the following characteristics:

1. Plants of the new *Diascia* are more freely branching than plants of the male parent selection.
2. Plants of the new *Diascia* have stronger lateral branches than plants of the male parent selection.

Plants of the new *Diascia* can be compared to plants of the cultivar Diastina, disclosed in U.S. Plant Pat. No. 13,932. In side-by-side comparisons conducted in Lüdinghausen, Germany, plants of the new *Diascia* differed from plants of the cultivar Diastina in the following characteristics:

1. Plants of the new *Diascia* were more compact than plants of the cultivar Diastina.
2. Plants of the new *Diascia* were more upright than plants of the cultivar Diastina.
3. Plants of the new *Diascia* had narrower leaves and longer leaf petioles than plants of the cultivar Diastina.
4. Plants of the new *Diascia* flowered about two weeks earlier than plants of the cultivar Diastina.
5. Plants of the new *Diascia* and the cultivar Diastina differed in flower color as plants of the cultivar Diastina had lighter colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Diascia.*

The photograph on the first sheet is a close-up view of typical flowering stems of 'Sumdia 02'.

The photograph on the second sheet comprises a top perspective view of a typical flowering plant of 'Sumdia 02' grown in a container.

DETAILED BOTANICAL DESCRIPTION

The aforementioned photographs and following observations and measurements describe plants grown in Lüdinghausen, Germany, in a glass-covered greenhouse during the spring with day temperatures about 15 to 18° C., night temperatures about 12° C., and light levels about 20,000 to 30,000 lux. Plants were grown for about 12 weeks in 12-cm containers; plants were pinched one time.

Color references are made to The Royal Horticultural Society Colour Chart, 2001 Edition, except where general terms of ordinary dictionary significance are used.

Botanical classification: *Diascia elegans* cultivar Sumdia 02.

Parentage:

*Female parent.*—Proprietary seedling of *Diascia elegans* identified as code number 14, not patented.

*Male parent.*—Proprietary seedling of *Diascia elegans* identified as code number 2, not patented.

Propagation:

*Type cutting.*—Terminal vegetative cuttings.

*Time to initiate roots, summer.*—About 7 days at 18° C.

*Time to initiate roots, summer.*—About 8 to 9 days at 18° C.

*Time to produce a rooted young plant, summer.*—About 16 days at 18° C.

*Time to produce a rooted young plant, winter.*—About 24 days at 18° C.

*Root description.*—Fine, fibrous; 162A in color.

*Rooting habit.*—Freely branching; moderately dense.

Plant description:

*Form.*—Compact, upright and outwardly spreading plant habit. Freely branching with lateral branches potentially forming at every node. Moderately vigorous growth habit.

*Plant height.*—About 20 to 25 cm.

*Plant diameter.*—About 35 to 45 cm.

*Lateral branches (peduncles).*—Length: About 20 cm. Diameter: About 1 mm. Internode length: About 1.5 to 4 cm. Texture: Smooth, glabrous. Color: 144A.

*Foliage description.*—Arrangement: Opposite, simple. Length: About 1.8 to 2 cm. Width: About 1.4 to 1.6 cm. Shape: Ovate to lanceolate. Apex: Acute. Base: Cordate. Margin: Serrate. Texture, upper and lower surfaces: Smooth, glabrous. Venation pattern: Pinnate. Color: Developing foliage, upper surface: 146A. Developing foliage, lower surface: 147C. Fully expanded foliage, upper surface: 146A. Fully expanded foliage, lower surface: 148B. Venation, upper surface: 146A. Venation, lower surface: 144A. Petiole length: About 5 to 7 mm. Petiole diameter: About 1 mm. Petiole texture, upper and lower surfaces: Smooth, glabrous. Petiole color, upper and lower surfaces: 144A.

Flower description:

*Flower type and habit.*—Solitary zygomorphic flowers arranged on terminal racemes. Five modified petals fused at base: two upper (banner) petals, two lateral petals, and one larger lower lip petal. Flowers not persistent. Flowers face upright to outwardly.

*Quantity.*—Freely flowering; typically about 12 buds and flowers per lateral branch.

*Natural flowering season.*—Long flowering period, plants flower continuously from early spring until the fall in Germany.

*Time to flower.*—Early flowering; plants begin flowering about six weeks after pinching.

*Flower longevity on the plant.*—About four to five days.

*Fragrance.*—Not detected.

*Inflorescence size.*—Length: About 10 to 12 cm. Width: About 3 to 4 cm.

*Flower size.*—Diameter: About 1.7 to 1.9 cm. Depth: About 1.8 to 2 cm.

*Flower buds.*—Length: About 2 mm. Diameter: About 2 mm. Shape: Ovoid. Color: 141B.

*Petals.*—Quantity/arrangement: Five modified petals fused at base: two upper (banner) petals, two lateral petals, and one larger lower lip petal. Base of banner petals with concave yellow eyespots; lower surfaces of lateral petals modified into nectar spurs; and lower lip petal convex forming a rougly horizontal insect landing platform. Length: Banner petals: About 6 mm. Lateral petals: About 7 mm. Lower lip petal: About 1.1 cm. Width: Banner petals: About 8 mm. Lateral petals: About 7 mm. Lower lip petal: About 1.2 cm. Lateral petal spur: Length: About 6 mm. Diameter, at petal attachment: About 2 mm. Shape, all petals: Obovate. Apex, all petals: Rounded. Margin, all petals: Entire. Texture, all petals, upper and lower surfaces: Smooth, glabrous. Color, all petals: When opening, upper surface: 44D. When opening, lower surface: 43D. Fully opened, upper surface: 45D; color becoming closer to 47A with development. Fully opened, lower surface: 44C. Nectar spurs: 46A to 53A with development. Eyespot on banner petals: Close to 7A.

*Sepals.*—Arrangement/appearance: Single whorl of five sepals fused at base; star-shaped. Length: About 3 to 4 mm. Width: About 1 mm. Shape: Lanceolate. Apex: Acute. Base: Truncate. Margin: Entire. Texture, upper and lower surfaces: Smooth, glabrous. Color, upper and lower surfaces: 147B.

*Pedicels.*—Length: About 1.4 to 1.6 cm. Width: About 0.5 mm. Angle: About 45° from vertical. Strength: Moderately strong. Texture: Smooth, glabrous. Color: 144A.

*Reproductive organs.*—Stamens: Quality per flower: About three or four. Anther shape: Round. Anther length: Less than 0.5 mm. Anther color: 9A. Pollen amount: Abundant. Pollen color: 9A. Pistils: Quantity per flower: One. Pistil length: About 2 mm. Style length: Less than 0.1 mm. Style color: 138D. Stigma shape: Rounded. Stigma color: 138D. Ovary color: 138D.

*Fruit/seed.*—Fruit and seed production has not been observed.

Disease/pest resistance: Plants of the new *Diascia* have not been noted to be resistant to pathogens or pests common to *Diascia*.

Temperature tolerance: Plants of the new *Diascia* have been observed to tolerate temperatures from 0 to 40° C.

It is claimed:

1. A new and distinct cultivar of *Diascia* plant named 'Sumdia 02', as illustrated and described.

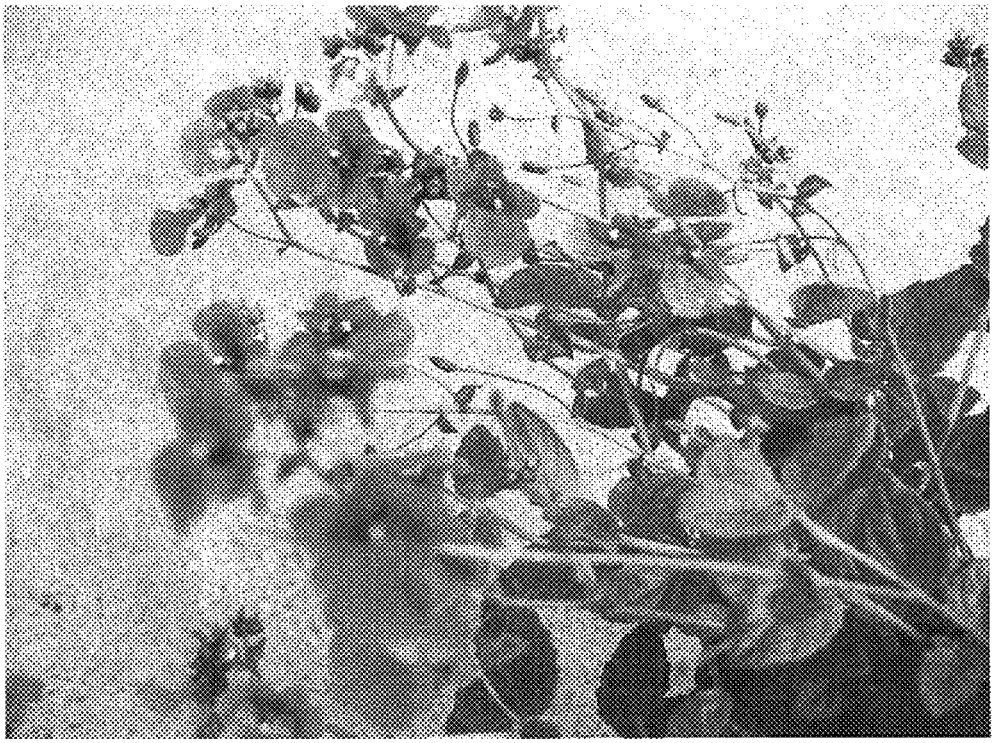

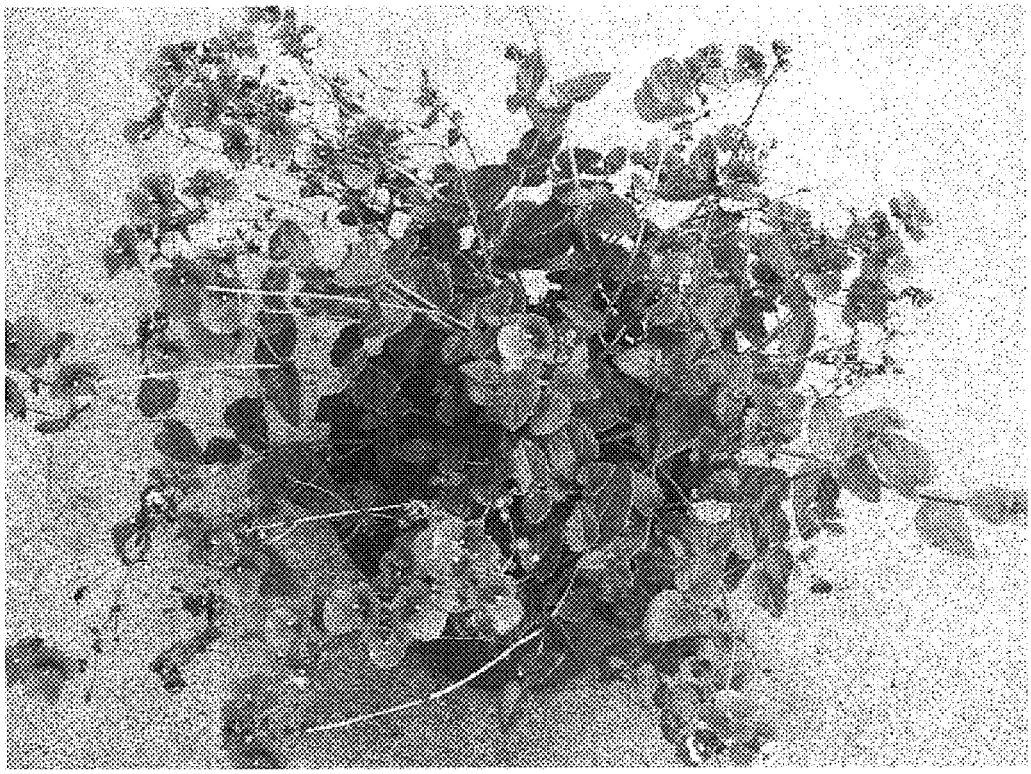

* * * * *